United States Patent
Farber et al.

(10) Patent No.: US 11,229,622 B2
(45) Date of Patent: Jan. 25, 2022

(54) COSMETOLOGICAL AND PHARMACEUTICAL COMPOSITION BASED ON COMBINATORIAL QUERCETIN DERIVATIVE

(71) Applicants: Boris Farber, Brooklyn, NY (US); Sof'ya Farber, Brooklyn, NY (US); Artur Viktorovich Martynov, Kharkov (UA)

(72) Inventors: Boris Farber, Brooklyn, NY (US); Sof'ya Farber, Brooklyn, NY (US); Artur Viktorovich Martynov, Kharkov (UA)

(*) Notice: Subject to any disclaimer, the term of this patent is extended or adjusted under 35 U.S.C. 154(b) by 9 days.

(21) Appl. No.: 16/771,355

(22) PCT Filed: Jun. 16, 2017

(86) PCT No.: PCT/RU2017/000425
§ 371 (c)(1),
(2) Date: Jun. 10, 2020

(87) PCT Pub. No.: WO2018/231092
PCT Pub. Date: Dec. 20, 2018

(65) Prior Publication Data
US 2021/0205263 A1    Jul. 8, 2021

(51) Int. Cl.
| | | |
|---|---|---|
| *A61K 31/353* | (2006.01) | |
| *A61P 17/02* | (2006.01) | |
| *A61K 8/02* | (2006.01) | |
| *A61K 8/49* | (2006.01) | |
| *A61K 8/67* | (2006.01) | |
| *A61K 9/127* | (2006.01) | |
| *A61K 9/51* | (2006.01) | |
| *A61K 31/593* | (2006.01) | |
| *A61K 47/24* | (2006.01) | |
| *A61Q 19/08* | (2006.01) | |
| *C04B 40/04* | (2006.01) | |
| *C40B 40/04* | (2006.01) | |

(52) U.S. Cl.
CPC .......... *A61K 31/353* (2013.01); *A61K 8/0241* (2013.01); *A61K 8/498* (2013.01); *A61K 8/67* (2013.01); *A61K 9/127* (2013.01); *A61K 9/51* (2013.01); *A61K 31/593* (2013.01); *A61K 47/24* (2013.01); *A61P 17/02* (2018.01); *A61Q 19/08* (2013.01); *C40B 40/04* (2013.01); *A61K 2800/413* (2013.01)

(58) Field of Classification Search
CPC .... A61K 31/353; A61K 8/0241; A61K 8/498; A61K 8/67; A61K 9/127; A61K 9/51; A61K 31/593; A61K 47/24; A61K 2800/413; A61P 17/02; A61Q 19/08; C40B 40/04
See application file for complete search history.

(56) References Cited

U.S. PATENT DOCUMENTS 5,043,321 A * 8/1991 Baertschi ........... A61K 38/2242
514/9.7

OTHER PUBLICATIONS

Ravishkar et al. (Published Jun. 2016; RSV Adv., 2016, 64544-64556).*
Bridson (Master Thesis 2007).*

* cited by examiner

*Primary Examiner* — Shirley V Gembeh
(74) *Attorney, Agent, or Firm* — Daniel M. Cohn; Howard M. Cohn

(57) ABSTRACT

The basis to develop a cosmetic and pharmaceutical composition based on a combinatorial derivative of quercetin in the form of nanoparticles (liposomes) for the treatment of atherosclerosis and its complications, as well as hypertension, for rejuvenating the body and healing wounds.

The problem is solved by obtaining a cosmetic and pharmaceutical composition based on a combinatorial quercetin derivative, characterized in that the modified combinatorial quercetin derivative is represented as a combinatorial library (mixture) of quercetin derivatives obtained by simultaneous combinatorial modification of quercetin with at least two alkylating and acylating modifiers in the combinatorial reaction synthesis to obtain the maximum number of different derivatives of quercetin, and as biologically active substances, a whole combinatorial mixture of quercetin derivatives is used without separation into individual components to create cosmetic and pharmaceutical compositions.

15 Claims, 5 Drawing Sheets

COSMETOLOGICAL AND PHARMACEUTICAL COMPOSITION BASED ON COMBINATORIAL QUERCETIN DERIVATIVE

TECHNICAL FIELD

The invention relates to combinatorial chemistry, pharmaceuticals and cosmetology. It allows you to synthesize new combinatorial libraries of quercetin for use in pharmaceutical industry and in cosmetology, including to create means of rejuvenating processes of the body, treating human diseases such as atherosclerosis and its complications like hypertension.

STATE OF THE ART

Combinatorial chemistry, the methodology of organic chemical synthesis, is aimed at the synthesis of a large array of chemical compounds of the same type (combinatorial libraries) in the fastest and most economical way. Also using specific approaches and technologies. The need for the synthesis of extensive combinatorial libraries arose in the 1990s and was dictated by the requests of those industries where the search for substances with useful properties is often more efficient by conducting empirical enumeration of properties on large samples of compounds of the same type.

The basis for the development of a new direction in chemical synthesis was the solid-phase peptide synthesis proposed by R. Merrifield. Specifically, intensive methods of combinatorial chemistry are used in pharmaceuticals (for the design of new drugs), in the search for effective catalysts (polymerization, etc.), and the design of nanomaterials. For testing combinatorial libraries, automated robotic systems have been developed whose performance reaches 100 thousand samples per day (the so-called high-performance screening).

In practice, combinatorial chemistry is a set of techniques and methods for combining diverse initial chemical reagents to obtain the most diverse arrays of chemical products by conducting tens, hundreds, and sometimes thousands of parallel chemical transformations with the formation of a huge number of final products. Combinatorial chemistry solves problems rarely arising in classical chemical synthesis, namely, to quickly synthesize many substances, usually complex in structure and sufficiently pure.

The development of new economical and high-speed technologies for parallel synthesis and parallel purification of substances is achieved in a variety of ways. Instead of the standard liquid-phase synthesis (one substance in one vessel at a time), a lot of syntheses are tested simultaneously. For example, in a plastic plate with many cells, where the substances are introduced by multichannel pipettes.

Instead of boiling with heating under reflux, we use the heating of many sealed capsules (in a cellular thermostat or microwave oven). To filter many substances we are using "filter vessels" (for example, dies with a porous bottom). Evaporation is carried out by vacuum freezing of the solvent from centrifuged dies (to prevent foaming).

For purification using methods of parallel chromatography, combining in blocks of many chromatographic columns. In the methods of liquid-phase combinatorial chemistry, they try to use only those reactions that proceed in high yields and require minimal effort to purify the substances.

In order to achieve a wider variety of products, conventional two-component reactions are replaced by multicomponent ones. A powerful technology of combinatorial chemistry is solid-phase synthesis—carrying out reactions on a modified polymer substrate. In this case, a complex molecule (for example, a polypeptide of the desired sequence or a complex heterocyclic compound) is immobilized ("built up") on the surface of the polymer during the sequence of reactions, and then, at the final stage, it is cleaved from the solid substrate due to any chemical transformations. Therefore, reactions can be carried out with a large excess of reagent, washing the latter from the polymer with the target substance and reducing the synthesis to the principle of "tea bag" (porous bags with polymer granules are successively placed in glasses with reagents).

A new technology is the replacement of solid polymers with perfluorinated liquids (not miscible with water and standard solvents). For immobilization (transfer of the substance to the perfluorinated phase), an extended perfluoroalkyl moiety is attached to the molecule of the starting reagent. This allows the synthesis in emulsions, followed by separation of the liquid phases. The combined method of combinatorial chemistry is the use of solid-phase reagents (oxidizing agent, acid, base are immobilized on a polymer). Excess solid reagent is added to the solutions of substances, and then separated by filtration. Another technique is the use of so-called scavengers—a modified polymer is introduced into the solution, which selectively removes excess reagent from the reaction mixture, taken in excess. Programmed industrial robots are increasingly being used, performing a sequence of routine, uniform procedures for the isolation and purification of substances (automatic synthesizers). The effectiveness of combinatorial chemistry has been proven by the examples of the discovery of new drugs and catalysts.

Our proposed scheme for the synthesis of combinatorial derivatives based on polyfunctional source molecules by reaction with two or more source modifiers without subsequent separation and isolation of each individual derivative is unique. Our process showed an increase in biological activity from two to 300 times for different source molecules: polymyxin, gentamicin, streptomycin, individual oligomeric RNA and DNA, polysaccharides, proteins, quercetin and many other substances. An important innovation in this approach is the correct calculation of the molar ratio of the number of reagents: both the initial polyfunctional compound (in this case, quercetin) and modifiers.

With the correct ratio of components, the maximum possible combination of derivatives is formed. This mixture is not a classical solution or a mixture after synthesis, but rather an aqueous solutions forms supramolecular structures with each other in arbitrary positions and behaves like the original quercetin, but with a more pronounced biological activity and prolonged action. The formation of supramolecular structures can be traced by the absence of separation of the band of the combinatorial derivative at the chromatographic peak: any changes in the separation conditions could not lead to separation of the mixture, while in the H1 NMR spectrum there was obvious chaos from the absorption bands of hydrogen of both methyl groups of the acetic acid residue and ethyl groups the remainder of succinic acid and hydrogens not substituted phenyl hydroxyls. Thus, this combinatorial supramolecular structure behaves in a completely different way, exhibits new physicochemical properties and biological activity in lower concentrations and much longer than the original quercetin.

Quercetin

Protecting the brain from ischemic damage and improving the functional outcome of ischemic stroke are two of the main tasks of modern neurology. In addition, with stroke, the prevention and treatment of cardiovascular disorders is necessary. With this in mind, the search for drugs with a multimodal effect is justified, which will expand the choice and treatment options for cerebral stroke and its complications. These drugs include the drug, Corvitin (Borshchagovsky Chemical-Pharmaceutical Plant, Ukraine, Kiev), which allows you to immediately act on various parts of the pathobiochemical process.

Quercetin, the active substance of the substance, it exhibits the properties of a modulator of the activity of various enzymes, which involve in the degradation of phospholipids, affecting free radical processes. Quercetin responsible for biosynthesis intracellular nitric oxide, proteinases and others enzymes, which is manifested by cardioprotective action in cardiac ischemia and during reperfusion myocardial lesions.

Corvitin also exhibits antioxidant and immunomodulating properties, and inhibits thrombogenesis. The drug restores regional blood circulation and microcirculation without noticeable changes in vascular tone, increasing the reactivity of microvessels. Corvitin normalizes cerebral hemodynamics in ischemic lesions, and reduces the asymmetry coefficient of cerebral blood flow in ischemic stroke. These qualities of the drug are especially important in the treatment of patients with stroke and its cardiovascular complications. This is especially true when the doctor is faced with the question of how to treat such patients. Since many cerebral vasoactive drugs have a known side effect, the robbery syndrome, they cannot be used in the treatment of stroke patients with cardiovascular complications.

The results of clinical and neurological studies indicate the safety and high efficiency of Corvitin in the treatment of patients with ischemic stroke and cardiovascular disorders. The drug can be used in patients with cardiovascular complications with ischemic stroke as an add on to the basic treatment. It was established the beneficial effect of the drug in a daily dose of 0.5 g for the acute ischemic stroke with different stages of severity of the disease.

The use of the drug Corvitin significantly increases the level of social adaptation in patients in the acute period of cerebral infarction. Significant improvement in cognitive functions and psychoemotional state was noted in patients receiving Corvitin with standard therapy. The simultaneous use of Corvitin along with standard therapy leads to an improvement in the quality of life. Corvitin helps to normalize the balance between excitatory neuroamino acids of the nervous system and inhibit its function.

Obtaining combinatorial derivatives with a range of physicochemical properties will allow both prolonging the action of quercetin, expanding the spectrum of its action, and increasing its bioavailability.

Chlorophyllipt

Chlorophyllipt is a cuprophyllin obtained from chlorophyll of the eucalyptu. It's intended for use as an antimicrobial agent for the treatment of staphylococcal infections. It is produced in the form of alcohol solutions for oral and intravenous administration (after dilution with a physiological solution). Recently, a number of new properties have been revealed in chlorophyllipt, previously unknown. In particular, anti-inflammatory effect and anti-allergic properties. The data obtained indicate that including chlorophyllipt in the complex treatment of patients with diabetes mellitus, leads to a pronounced neutralizing effect on aggressive autoimmune processes.

It is known that small- and medium-molecular circulating immune complexes (CICs) along with microbes, are an active complement activation factor, accompanied by the formation of anaphylotoxins and factors with cytolytic properties. In addition, the interaction of immune complexes with polymorphonuclear leukocytes leads to the release of active forms of oxygen, nitric oxide, kati proteins, lysosomal lytic enzymes into the intercellular space. These active substances act destructively on the tissue. Aggressive factors are also autoantibodies to collagen and elastin and TNFα, capable of inducing degenerative processes in the tissue.

Massive production of pro-inflammatory cytokines and superoxide radicals by polymorphonuclear leukocytes and by mononuclear cells in situ contributes to the development of inflammation and increased exudation from blood plasma of cellular and humoral factors, which has effect of lytic properties. In addition, immune complexes and cytokines, inducing platelet aggregation, contribute to the formation of microthrombi that impede capillary blood flow, which, in turn, leads to tissue ischemia and contributes to the development of atherosclerosis and its complications. In addition this causes the activation of platelets, polymorphonuclear leukocytes, mononuclear cells, lymphocytes by microbes and their toxins, as well as the entry of various pro-inflammatory factors into the general bloodstream. This entry then induces a generalized inflammatory reaction that negatively affects the general clinical status of patients and their immunoreactivity.

In patients with complications of atherosclerosis based on immune inflammatory reaction as one of the etiological factors that received intravenous chlorophyllipt in complex therapy, there is a significant decrease in exoproduction by cells of superoxide radicals. Additionally there is a decrease in the content of pro-inflammatory cytokines in the blood serum: IL-1β, IL-6, TNFα compared with patients who did not receive chlorophyllipt in complex treatment.

When chlorophyllipt is included in the complex treatment of patients, a more dynamic decrease in the content of autoantibodies to collagen and elastin and CIC in the blood serum is observed compared to patients who did not receive chlorophyllipt. The inclusion of chlorophyllipt in the pharmaceutical composition for correcting the consequences of atherosclerosis can significantly improve the quality of life of patients, eliminate relapses of atherosclerosis and inhibit its further progression. The disadvantage of chlorophyllipt is its complete hydrophobicity. To solve this problem, we proposed the preparation of nanovesicular suspension forms with chlorophyllipt integrated into the membrane—liposomes and milk vesicles.

Cholecalciferol

Recent data confirm the relationship of atherosclerosis with osteoporosis, which indicates the parallel progression of these two diseases. Several epidemiological and clinical studies have shown that there is an relationship between hypovitaminosis D and cardiovascular diseases. Epidemiological and experimental studies have shown that low levels of vitamin D can play an important role in cardiovascular diseases, including coronary heart disease, congestive heart failure, valvular calcifications, stroke, hypertension, and cognitive impairment. Hypovitaminosis D is considered a risk factor for the development of atherosclerosis. Vitamin D deficiency leads to a change in vascular smooth muscle cells, endothelial dysfunction, and an increase in peroxidic oxidation of various autoimmune diseases. This is due to several immunosuppressive properties of the vitamin.

There is much ongoing research into the increasing role of vitamin D in immunopathology. More and more publications highlight vitamin D in the pathology of immune diseases, including allergic diseases, although the pathogenesis is still unclear. It was found that synthetic VDR agonists have antiproliferative, differentiated, antibacterial, immunomodulating and anti-inflammatory properties This can be used to treat various autoimmune diseases, such as rheumatoid arthritis, systemic lupus erythematosus, multiple sclerosis, type 1 diabetes, and Crohn's disease. Studies conducted in animal models of multiple sclerosis, insulin-dependent diabetes mellitus, inflammatory bowel diseases and transplantation, confirmed the hypothesis that 1 alpha, 25-(OH) 2D3 leads to increased function of T-suppressors. Furthermore, these data stimulate interest in the immunological role of vitamin D.

It was also found that 1,25-dihydroxyvitamin D3 delays cellular replicative aging in human mesenchymal stem cells while maintaining their multipotent power. In addition, pharmacological doses of 1,25-dihydroxyvitamin D3 (1.25 (OH) (2), D) prevent type 1 diabetes and obesity in mice by inducing immune modulation thereby directly affecting the pancreatic beta cells.

In the tissue of the pancreas, in particular in beta cells, as well as in the cells of the immune system, there are vitamin D receptors and vitamin D binding proteins. Vitamin D is thought to help maintain insulin secretion. In type 2 diabetes mellitus, vitamin D increases the sensitivity of cells to insulin and reduces inflammation in the tissues of the pancreas. Many preclinical studies confirm the role of vitamin D in the pathogenesis of both types of diabetes. So, patients with both types of diabetes have a higher level of hypovitaminosis D than healthy people. Clinical studies have confirmed that hypovitaminosis D is a risk factor for the development of insulin resistance regardless of the presence of obesity in children. Perhaps in the future it is necessary to focus on the therapeutic potential of vitamin D in the prevention and treatment of type 1 and type 2 diabetes mellitus, as well as its complications. The main questions have yet to be answered. Namely, can increasing the intake of vitamin D at maximum doses in healthy people reduce the risk of developing diabetes? Can it reduce the severity of the disease and its complications, including cardiovascular disease?

It was found that the activation of VDR in the kidneys prevents the manifestation of renal pathology. In vivo treatment with the doxercalciferol agonist (1-a-hydroxyvitamin D2) prevents kidney disease. The results show that in the treatment of vitamin D3 there are several mechanisms: the development of lung immunity, reduction of inflammation, reducing hyperplasia and increasing the effects of exogenous steroids. It has been found that the nuclear status of VDR can be a prognostic marker for lung cancer. There is a high prevalence of vitamin D deficiency in patients with diseases of the pulmonary intestinal tissue, and this is associated with a decrease in lung function. Thus, a deficiency of vitamin D contributes to the development of pulmonary fibrosis. It was revealed that D (3) inhibits the pro-fibrous phenotype of pulmonary fibroblasts and epithelial cells.

It has been established that the large intestine, mammary gland, prostate, macrophages, and skin have enzymatic mechanisms for the production of 1,25 dihydroxy D. Blood circulating 25-hydroxyvitamin D3 (25 [OH] D), most often used to assess the status of vitamin D, turns into the active hormone 1,25-dihydroxyvitamin D3 (1.25 [OH] 2 D), which, acting through VDR, inhibits cell proliferation in vitro, induces differentiation and apoptosis, as well as cell migration. Thus, both 25-hydroxyvitamin D3 (25 [OH] D) and 1,25 dihydroxyvitamin D3 (1,25 [OH] 2 D) can prevent cancer.

At the present stage, a number of studies confirm the role of vitamin D as a prophylactic and therapeutic agent against cancer. An insufficient level of 25-hydroxyvitamin D (25 (OH) D) is associated with an increased risk and unfavorable prognosis for several types of cancer. Through a meta-analysis of randomized trials, vitamin D supplements have been shown to reduce overall mortality and progression of melanoma. Epidemiological evidence suggests that low vitamin D levels can play a role in the onset and progression of breast, lung, colon, and prostate cancer Glandular cancer, as well as malignant lymphoma. Calcitriol has a strong antiproliferative effect in cancers of the prostate, mammary gland, colon, head, neck, and lung It also had a strong effect on the lymphatic system, leukemia, and myeloma. Antiproliferative effects are manifested both in vitro and in clinical settings. The mechanism of these effects associated with G0/G1 blockade, induction of apoptosis, differentiation and modulation of the growth factor in tumor cells. In addition to a direct effect on tumor cells, recent data convincingly confirms the hypothesis of stromal effects of vitamin D analogues (for example, a direct effect on the vasculature of a tumor).

Giovannucci et al., Who developed and approved estimates of serum 25 (OH) cholecalciferol levels and reported that among more than 40,000 individuals in the study, an increase in 25 (OH) cholecalciferol levels to 62.5 ng/ml was associated with a reduction in cancer risk in the head, neck, esophagus, and pancreas. In addition, was acute leukemia was reduced by more than 50%. Recently, a large number of studies have been conducted on VDR genes (fragment polymorphism) for various types of cancer. It has been suggested that VDR polymorphism can affect both the risk of cancer and its prognosis. It was also confirmed the effect of vitamin D on the different areas of neuromuscular functions. According to our studies, vitamin D supplements increase neuromuscular or neuroprotective function, which may explain the mechanism of the role of vitamin D in reducing falls and fractures. Vitamin D has been found to have potential antimicrobial activity, decreasing susceptibility to infection in patients with atopic dermatitis. Vitamin D is able to regulate local immune-inflammatory reactions, presenting great potential for understanding the pathogenesis and treatment of chronic inflammatory dermatitis. The risk of contracting an infection is reduced through several mechanisms: stimulation of innate immunity by modulating the production of antimicrobial peptides (AMPs) and the effect on cytokines. According to research, these mechanisms play an increasingly important role in the development of atopic dermatitis, psoriasis, vitiligo, acne and rosacea.

Vitamin D3 is considered as the main indicator of vitamin D availability: the plasma concentration of 25-hydroxyvitamin D and parathyroid hormone, as well as the presence or absence of clinical manifestations of rickets. Thus, cholecalciferol or vitamin D3 is one of the most interesting candidates for the development of compositions for the prevention and treatment of atherosclerosis and its complications. Vitamin D3, like chlorophyllipt, is a hydrophobic compound and we proposed to introduce it into vesicles (into liposome phospholipids, milk vesicles, and polysorbate-based polymer vesicles).

Terminology

Formylation is the process of attaching the formic acid residues to amino groups, alcohol groups with the formation of the aldehyde group residues. There are many named reactions of formylation (Duff reaction, Hatterman reaction, Guben-Gösch reaction, Hatterman-Koch reaction)

Acylation—the introduction of the acyl residue of RCO— (acyl) into the organic compound, as a rule, by replacing the hydrogen atom, the introduction of the residue of acetic acid CH3CO— is called acetylation, benzoic $C_6H_5CO$—benzoylation, formic HCO—formylation. Depending on the atom to which the acyl residue is attached, C-acylation, N-acylation, O-acylation are isolated. Acid halides and acid anhydrides are used as acylating agents.

Alkylation—the introduction of an alkyl substituent in an organic compound molecule. Typical alkylating agents are alkyl halides, alkenes, epoxy compounds, alcohols, less often aldehydes, ketones, esters, sulfides, diazoalkanes. The alkylation catalysts are mineral acids, Lewis acids, and also zeolites. Alkylation is widely used in the chemical and petrochemical industries.

Combinatorial synthesis—synthesis by methods of combinatorial chemistry, includes the simultaneous reaction between three or more reagents with the formation of a combinatorial synthesis product, consisting of dozens of derivatives. These derivatives are then separated chromatographically, confirm their structure and study the biological activity.

Simultaneous combinatorial modification by two modifiers—if during reaction of combinatorial synthesis a multifunctional molecule is used, which has more than two groups available for modification in the reaction, than two modification agents are introduced immediately, for example, acetic anhydride and succinic anhydride. As a result of the reaction, a mixture of acylated derivatives in different positions—acetyl-succinyl derivatives is formed.

The combinatorial library [lat. combinare—connect, combine; Greek biblion—book and theke—repository]—a set of a large number of various chemical compounds, proteins, genes or oligonucleotides, allowing you to quickly search for target genes or proteins. For example, a kit consisting of millions of different chemicals, or a set of recombinant DNA molecules, obtained by incorporating various antibodies into the light and heavy chains of cDNAs.

Vicianosylated quercetin derivatives are known [U.S. Pat. No. 3,888,842]. These derivatives accumulate better in the walls of capillaries and larger vessels, they also stay there longer. The disadvantage of patentable derivatives is the artificial vicianosyl group, which is quite toxic and is not metabolized until complete assimilation by the body. The proposed derivatives are completely xenobiotic, do not represent combinatorial mixtures in the form of supramolecular structures, and cannot "adapt" to the individual characteristics of the body like combinatorial systems. In addition, the derivatives patented in the prototype did not show any antiatherosclerotic or hypotensive effect.

Another analogue is known—composition and methods for the prevention of cardiovascular diseases [US Patent application US 2012/0100123 A1 and U.S. Pat. No. 9,278, 109 B2], the composition is based on a mixture of CoQ10 vitamins, omega fatty acids, natural bioflavonoids (including quercetin), natural vitamin E, amino acids, minerals, olive oil, lecithin, B vitamins, and antioxidants.

The difference between this composition and our proposed one is the absence of chlorophyllipt, a combinatorial mixture of quercetin and vitamin D3 in the form of nanoparticles (liposomes or milk lipid vesicles). These components are the core of our composition and provides an obvious pharmacological effect in contrast to the composition previously proposed in the application.

Moreover, the prototype composition also contains bioflavonoids (including quercetin) and vitamins (except for group D vitamins) The double modification of quercetin allows one to obtain 92 derivatives that together form a more complex supramolecular structure (superstructure); the biological properties of which significantly exceed those of pure quercetin, and this structure is able to adapt to changing external conditions.

DISCLOSURE OF INVENTION

The basis of the invention is the task to develop a cosmetic and pharmaceutical composition based on a combinatorial derivative of quercetin for the treatment of atherosclerosis and its complications, as well as hypertension, body rejuvenation, creation of compositions for wound healing.

The problem is solved by obtaining a cosmetic and pharmaceutical composition based on a combinatorial quercetin derivative, wherein the modified combinatorial quercetin derivative is represented as a combinatorial mixture of quercetin derivatives obtained by simultaneous combinatorial modification of quercetin with at least two alkylating and acylating modifiers in a molar ratio of components (quercetin:1st modifier:2nd modifier=92:155:155) in the combinatorial synthesis reaction and to obtain the maximum number of different derivatives of quercetin, and as biologically active substances, a whole combinatorial mixture of derivatives of quercetin is used without separation into individual components to create cosmetic and pharmaceutical compositions.

For any other molar ratios of the components, the number of derivatives will not be maximum (92 molecules) and the supramolecular structure will not form. Based on the combinatorial derivatives of quercetin, a pharmaceutical and cosmetic composition is obtained, characterized in that the active ingredients in the lipophilic phase are the combinatorial derivative of quercetin, a thick extract of chlorophyllipt and cholecalciferol with this ratio of components, wt. %:
quercetin combinatorial derivatives according to claim 1. 0.5-20
excipient 50-70
thick chlorophyllipt extract 2-7
cholecalciferol 1.0-3.0
excipients up to 100,
the composition is emulsified by known methods to obtain the desired size of the nanoparticles (liposomes). At the same time, the resulting combinatorial mixture of quercetin derivatives is not purified to separate components, but is used entirely as the main active substance to prevent adaptation of the body (slippage effect).

Double modification of quercetin leads to an increase in the number of its derivatives, which manifests itself in an increase in its pharmacological activity, an expansion of the spectrum of action and prolongation of its presence in the body. The super effect of such a derivative of quercetin and compositions based on it is a high anti-atherosclerotic activity in vivo, reduction of atherosclerotic plaques, including calcined, which so far has not been possible to achieve with other drugs due to a complex anti-inflammatory effect, as well as a new effect—pronounced hypotensive.

PHARMACEUTICAL COMPOSITIONS

Figure 1:
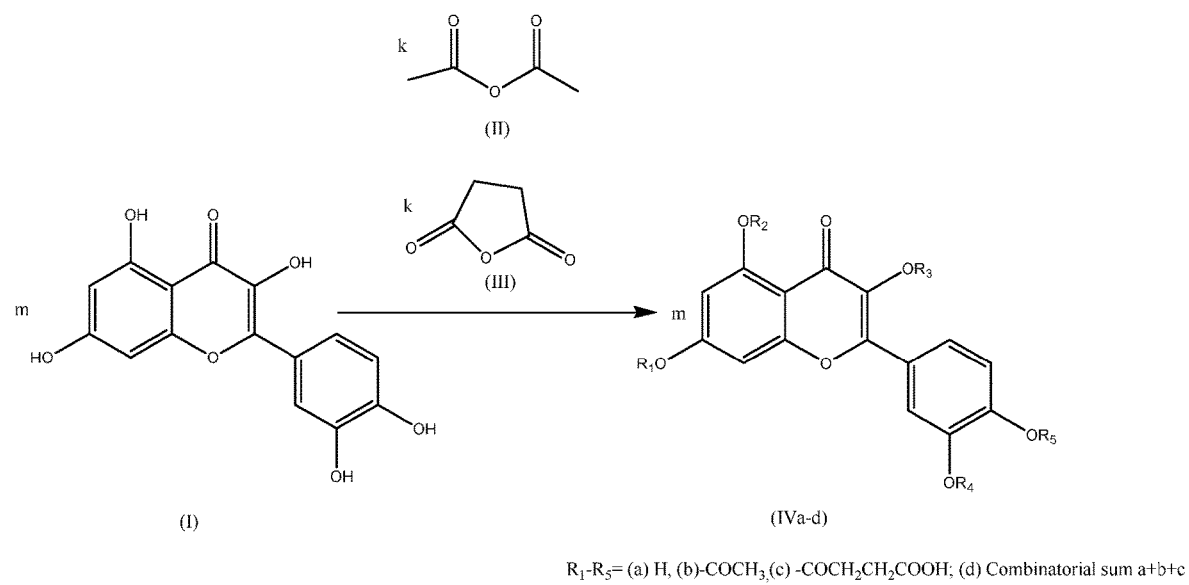
FIG. 1. Chemical synthesis scheme for combinatorially modified quercetin derivatives.

Various methods of preparing a patentable pharmaceutical composition (PFC) can be used. The PFC composition can be given orally or can be administered by intravascular, subcutaneous, intraperitoneal injection, in the form of an aerosol, by ocular route of administration, into the bladder, topically, and so on. For example, inhalation methods are well known in the art. The dose of the therapeutic composition will vary widely depending on the specific antimicrobial PFC administered, the nature of the disease, frequency of administration, route of administration, clearance of the agent used from the host organism and the like. The initial dose may be higher with subsequent lower maintenance doses. The dose can be administered with a frequency of once a week or once every two weeks. The dose can also be divided into smaller doses and administered once or several times a day, twice a week, and so on to maintain an effective dose level.

In many cases, a higher dose will be needed for oral administration than for intravenous administration. PFCs can be included in many therapeutic compositions. More specifically, the PFCs of the present invention can be incorporated into pharmaceutical compositions in combination with suitable pharmaceutically acceptable carriers or diluents, and can be incorporated into preparations in solid, semi-solid, liquid or gaseous forms, such as capsules, powders, granules, ointments, creams, foams, solutions, suppositories, injections, forms for inhalation use, gels, microspheres, lotions and aerosols. As such, the administration of the compounds can be carried out in various ways, including oral, buccal, rectal, parenteral, intraperitoneal, intradermal, transdermal, intratracheal administration and so on. The PFCs of the invention can be distributed systemically after administration or can be localized using an implant or other composition that holds the active dose at the site of implantation.

The PFCs of the present invention can be administered alone, in combination with each other, or they can be used in combination with other known compounds (e.g. clopidogrel, anti-inflammatory agents, and so on). In pharmaceutical dosage forms, the compounds may be administered in the form of their pharmaceutically acceptable salts. The following methods and excipients are given as examples only and are in no way limiting.

For oral administration preparations, the compounds can be used alone or in combination with suitable additives for the manufacture of tablets, powders, granules or capsules For example, with conventional additives such as lactose, mannitol, corn starch or potato starch. It can also be combined with binding agents, such as crystalline cellulose, cellulose derivatives, gum arabic, corn starch or gelatins; with disintegrants such as corn starch, potato starch or sodium carboxymethyl cellulose; with lubricating agents such as talc or magnesium stearate, and, if desired, with diluents, buffering agents, moistening agents, preservatives and flavoring agents.

PFCs should be included in injectable compositions by dissolving, suspending or emulsifying them in an aqueous or non-aqueous solvent such as vegetable or other similar oils, synthetic aliphatic acid glycerides, esters of higher aliphatic acids or propylene glycol; and, if desired, with conventional additives such as solubilizers, isotonic agents, suspending agents, emulsifiers, stabilizers and preservatives. PFCs can be used in an aerosol composition for inhalation administration. The compounds of the present invention can be incorporated into suitable pressure propellants such as dichlorodifluoromethane, propane, nitrogen and the like. In addition, PFCs can be incorporated into suppositories by mixing with a variety of bases, such as emulsifying bases or water-soluble bases. The compounds of the present invention can be administered rectally using a suppository. The suppository may contain excipients such as cocoa butter, carbovaxes and polyethylene glycols, which melt at body temperature but are solid at room temperature.

Standard dosage forms for oral or rectal administration, such as syrups, elixirs and suspensions, where each unit dose, for example, a teaspoon, tablespoon, tablet or suppository, may contain a predetermined amount of a composition containing one or more compounds of the present invention. Similarly, unit dosage forms for injection or intravenous administration may contain the compound of the present invention in a composition in the form of a solution in sterile water, normal saline, or another pharmaceutically acceptable carrier. Implants for the sustained release of compositions are well known in the art. Implants are made in the form of microspheres, plates, and so on with biodegradable or non-biodegradable polymers. For example, lactic and/or glycolic acid polymers form a degradable polymer that is well tolerated by the host. An implant containing PFC according to the invention is placed close to the pathology site, so that the local concentration of the active agent is increased compared to other areas of the body. As used herein, the term "unit dosage form" refers to physically discrete units suitable for use as single doses for human and animal subjects, each unit containing a predetermined number of compounds of the present invention, which According to calculations, it is sufficient to provide the desired effect, together with a pharmaceutically acceptable diluent, carrier or excipient.

The descriptions of unit dosage forms of the present invention depend on the particular compound used, and the effect to be achieved, as well as the pharmacodynamics of the compound used in the host. Pharmaceutically acceptable excipients, such as excipients, adjuvants, carriers or diluents, are generally available. In addition, pharmaceutically acceptable excipients are generally available, such as pH adjusters and buffers, tonicity agents, stabilizers, wetting agents and the like. Typical doses for systemic administration range from 0.1 pg to 1000 milligrams per kg of subject body weight per administration. A typical dose may be one tablet to be taken two to six times per day or one capsule or tablet with prolonged release for administration once a day with a proportionally higher content of the active ingredient. The effect of prolonged release may be due to the materials of which the capsule is made, dissolving at different pH values, capsules providing a slow release under the influence of osmotic pressure or by any other known controlled release method.

It will be clear to those skilled in the art that dose levels may vary depending on the particular compound, the severity of the symptoms, and the subject's predisposition to side effects. Some of the specific compounds are more potent than others. Preferred doses of this compound can be readily determined by those skilled in the art in a variety of ways. The preferred method is to measure the physiological activity of PFC. One of the methods of interest is the use of liposomes as a vehicle for delivery. Liposomes fuse with the cells of the target region and ensure the delivery of liposome contents into the cells. The contact of liposomes with cells is maintained for a time sufficient for fusion, using various methods of maintaining contact, such as isolation, binding agents, and the like. In one aspect of the invention, liposomes are designed to produce an aerosol for pulmonary administration. Liposomes can be made with purified proteins or peptides that mediate membrane fusion, such as Sendai virus or influenza virus and so on.

Lipids can be any necessary combination of known liposome forming lipids, including cationic or zwitterionic lipids, such as phosphatidylcholine. The remaining lipids will usually be neutral or acidic lipids, such as cholesterol, phosphatidylserine, phosphatidylglycerol and the like. To obtain liposomes, we utilized the method described by Kato et al. (1991) J. Biol. Chem. 266: 3361.

Briefly, lipids and a composition for incorporation into liposomes containing peptides are mixed in a suitable aqueous medium. Usually in a salt medium, where the total solids content will be in the range of about 110 wt. %. After vigorous stirring for short periods of approximately 5-60 seconds, the tube is placed in a warm water bath at approximately 25-40° C. and this cycle is repeated approximately 5-10 times. The composition is then sonicated for a suitable period of time, typically approximately 1-10 seconds, and optionally further mixed with a vortex mixer. Then the volume is increased by adding an aqueous medium, usually increasing the volume by about 1-2 times, followed by agitation and cooling. The method allows to include supramolecular structures with high total molecular weight in liposomes. Also, instead of chlorophyllipt, dye cuprophillin, chlorophyllin can be used, and instead of cholecalciferol, its synthetic derivatives Compositions with Other Active Agents For use in the methods under consideration, the PFCs of the invention can be formulated with other pharmaceutically active agents, in particular other cardiotropic and antiatherosclerotic agents. Other agents of interest include a wide range of antianginal, antihypertensive, thrombolytic, anti-inflammatory agents known in the art. The classes of agents for the treatment of atherosclerosis and its complication are presented in standardized treatment protocols for this pathology and can be combined with patented PFC. Cytokines, such as interferon gamma, tumor necrosis factor alpha, interleukin 12, and so on, may also be included in the PFC composition of the invention. The present invention is further described by the following examples, which should not be construed as limiting the scope of the invention.

Example 1. Obtaining a Combinatorial Mixture of Quercetin (CMQ)

92 mM quercetin (I) is dissolved in 10 ml of dioxane, 155 mM succinic anhydride (III) and 155 mM acetic anhydride are added, the solution is stirred and heated under reflux for 20 minutes. The solution was poured into ampoules and lyophilized to remove solvent and acetic acid. The combinatorial mixture is used to obtain pharmaceutical compositions, study the structure, determine the biological activity. FIG. 1 shows a synthesis scheme for combinatorial derivatives of quercetin.

One parent quercetin molecule contains 5 modifiable phenolic hydroxyl groups.

Calculations of the number of moles of modifiers are carried out according to the combinatorics formulas: $m=4\times(3\times2^{n-2}-1)$; $k=n\times(2^n-1)$, where m is the number of different derivative molecules in the combinatorial mixture and the number of moles of quercetin for the reaction; n—the amount of phenolic hydroxides available for modification in the structure of quercetin (n=5); k is the number of moles of each modifier. Thus, having only one initial quercetin molecule and two modifiers after combinatorial synthesis, we obtain 92 combinatorial derivatives with different degrees of substitution, different positions of substituents and different permutations of modifier residues, not just as a mixture, but as a difficult to separate supramolecular mixture. Modifiers—succinic anhydride or acetic anhydride can be entered both simultaneously and sequentially—or first introduce succinic anhydride, warm the mixture under reflux for 20 minutes, and then introduce acetic anhydride and also warm the mixture for another 20 minutes. Similarly, in this reaction, maleic anhydride, aconitic anhydride, glutaric, phthalic anhydride and acetic anhydride, formic acid ethyl ester, monochloroacetic acid can be used as one of the modifiers instead of succinic anhydride, propiolactone, ethylene oxide and other low molecular weight alkylating substances (methyl chloride, ethyl chloride, propyl chloride). Due to the complexity of the obtained structure, NMR H1 spectra were determined only for three compounds—(I), (IVb), (IVc) on a Brucker 300 spectrometer.

H1 NMR for the starting quercetin: s: 10.68; 16.47; 10.18; 10.68; 16.77; 6.02; 5.94; d: 6.51; 9.48; m 6.5-7.0

For the HPLC, a Milichrom A-02 microcolumn chromatograph in a gradient of acetonitrile (5-100%)/0.1 M perchloric acid+0.5 M lithium perchlorate was used. The combinatorial derivative in the chromatogram (FIG. 4) gave one clear broadened peak and was not divided into components, although the retention time was different from both quercetin and its fully substituted derivatives. This indicated that complex supramolecular structures that were not separated chromatographically formed between different combinatorial derivatives (in our case, 92). This combinatorial derivative (CMQ) behaves similarly when separated in a thin layer (acetonitrile:water) and gives only one band, which does not coincide with any of the obtained derivatives.

Table 1 shows the results of screening of quercetin derivatives with different ratios of modifiers as urease inhibitors (using soya urease as an example). The starting quercetin is known to be a urease inhibitor with a moderate degree of inhibition (ED50=200 μg/ml). The test was carried out by a micromethod in a tablet on the ability of quercetin derivatives to inhibit the process of urea destruction by urease Ammonia evolution colored the solution in the wells green in the presence of a pH-sensitive indicator, the color intensity was determined spectrophotometrically on a StatFax-303 SF reader. Destruction of urea with urease. The effective concentration was determined by double dilutions until 50% inhibition of urease (ED50). The spectrophotometer error was 10%.

TABLE 1

Inhibitory ability against urease from the side of supramolecular combinatorial derivatives of quercetin obtained in the reaction with different molar ratio of modifiers

| No. p/p | The molar ratio of reagents * | | | ED50 with respect to urease, µg/ml, measurement error 10% |
|---|---|---|---|---|
| | m | k1 | k2 | |
| 1 | 92 | 930*** | 930*** | >400 |
| 2 | -//- | 465 | 465 | 200 |
| 3 | -//- | 155 | 155 | 1 |
| 4 | -//- | 77 | 77 | 50 |
| 5 | -//- | 39 | 39 | 200 |
| 6 | -//- | 19 | 19 | 200 |
| 7 | -//- | 10 | 10 | 100 |
| 8 | -//- | 5 | 5 | 200 |
| 9 | -//- | 2 | 2 | 200 |
| 10 | -//- | 1 | 1 | 200 |
| 13 | -//- | 0 | 0 | 200 |
| 14 | -//- | 930*** | 0 | >400 |
| 16 | -//- | 465 | 0 | 200 |
| 17 | -//- | 155 | 0 | |
| 18 | -//- | 77 | 0 | |
| 19 | -//- | 39 | 0 | |
| 20 | -//- | 19 | 0 | 100 |
| 21 | -//- | 10 | 0 | 100 |
| 22 | -//- | 5 | 0 | 200 |
| 23 | -//- | 2 | 0 | 200 |
| 24 | -//- | 1 | 0 | 200 |
| 25 | -//- | 0 | 1860*** | >400 |
| 26 | -//- | 1 | 930 | >400 |
| 27 | -//- | 0 | 465 | 200 |
| 28 | -//- | 0 | 155 | 200 |
| 29 | -//- | 0 | 77 | 200 |
| 30 | -//- | 0 | 39 | 200 |
| 31 | -//- | 0 | 19 | 200 |
| 32 | -//- | 0 | 10 | 200 |
| 33 | -//- | 0 | 5 | 200 |
| 34 | -//- | 0 | 2 | 200 |
| 35 | -//- | 0 | 1 | 200 |
| 36 | -//- | 1860*** | 1 | >400 |
| 37 | -//- | 930 | 1 | >300 |
| 38 | -//- | 465 | 2 | 200 |
| 39 | -//- | 155 | 5 | 200 |
| 40 | -//- | 77 | 10 | 200 |
| 41 | -//- | 39 | 19 | 200 |
| 42 | -//- | 19 | 39 | 200 |
| 43 | -//- | 10 | 77 | 200 |
| 44 | -//- | 5 | 155 | 200 |
| 45 | -//- | 2 | 465 | 200 |
| 46 | -//- | 1 | 930 | >400 |

* m is the number of moles of quercetin in the combinatorial synthesis reaction; K1 is the number of moles of succinic anhydride in the reaction; K2 is the number of moles of acetic anhydride in the reaction;
**ED50 µg/ml urease inhibition was determined by diluting the initial concentration of 400 µg/ml quercetin derivative;
***the maximum molar ratio at which all groups in quercetin are replaced, an excess of this ratio leads to the fact that unreacted modifiers remain in the reaction medium - succinic anhydride and acetic anhydride.

As can be seen from table 1, only with the calculated ratio of components, when the maximum number of different derivatives of quercetin is formed, a biological active and effective supramolecular structure (derivative 3 or CMQ) is formed, capable of inhibiting urease at a dose of 1 µg/ml by 50%, which is 3 orders of magnitude less than the initial dose of unmodified polymyxin. Other derivatives either did not differ from unmodified quercetin in their ability to inhibit urease, or were significantly less active. This indicates that with an optimal ratio of modifiers when all possible derivatives are formed in solution (92 variations of quercetin derivatives with different permutations and arrangements in substituents) a more complex supramolecular quasi-fluid structure with other properties and more than 3 orders of magnitude greater pharmacological activity is formed.

Example 2. Obtaining Fully Succinylated Quercetin (Control 1)

10 mM quercetin (I) is dissolved in 10 ml of dioxane, 50 mM succinic anhydride (III) is added, the solution is stirred and heated under reflux for 20 minutes. The solution is poured into ampoules and lyophilized NMR H1 pentasuccinyl quercetin (IVc): s: 7.63; 7.63; 7.03; 7.1; 7.6; m 2.59-2.71; 12.00-12.2; HPLC (Milichrom A-02; Gradient HClO4/LiClO4: AcCN 5-100%):

Example 3. Obtaining Fully Acetylated Quercetin (Control 2)

Figure 2:
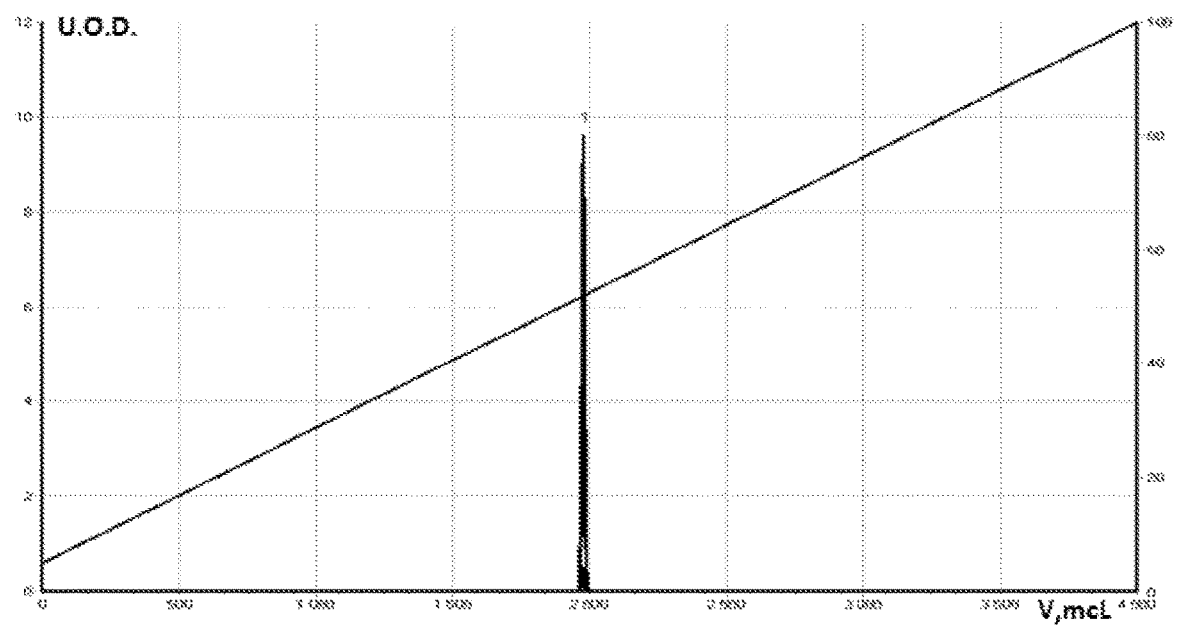
FIG. 2. HPLC (Milichrom A-02) quercetin (I), gradient A solution: 0.5 M lithium perchlorate/0.1 M perchloric acid, solution B: acetonitrile (B from 5% to 100%)
Figure 3:
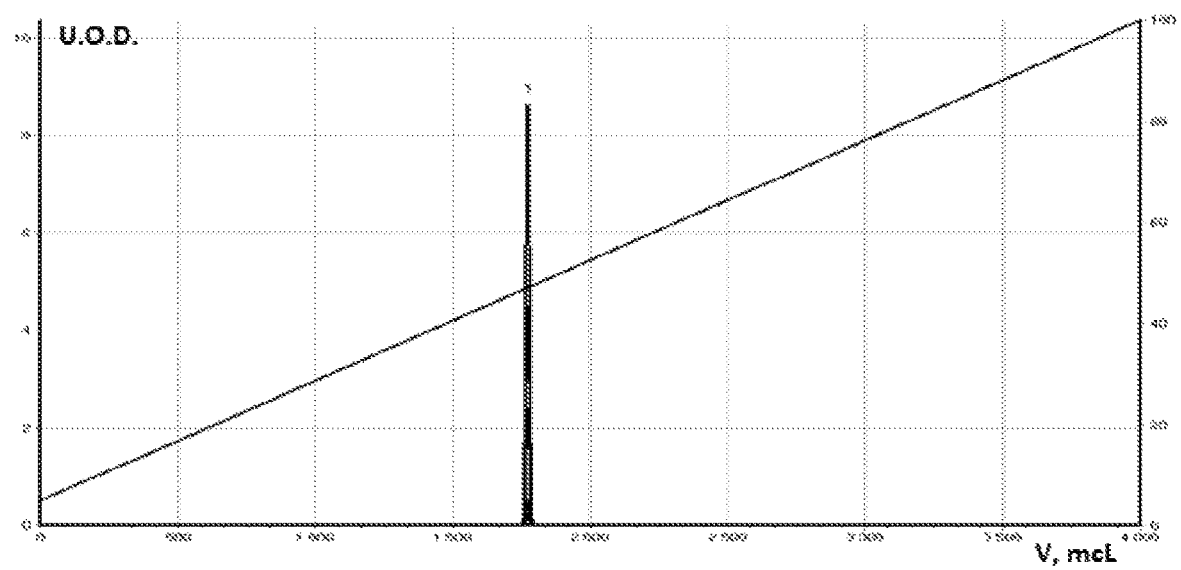
FIG. 3. HPLC (Milichrom A-02) of pentasuccinyl quercetin (IVc), gradient A solution: 0.5 M lithium perchlorate/ 0.1 M perchloric acid, solution B: acetonitrile (B from 5% to 100%)
Figure 4:
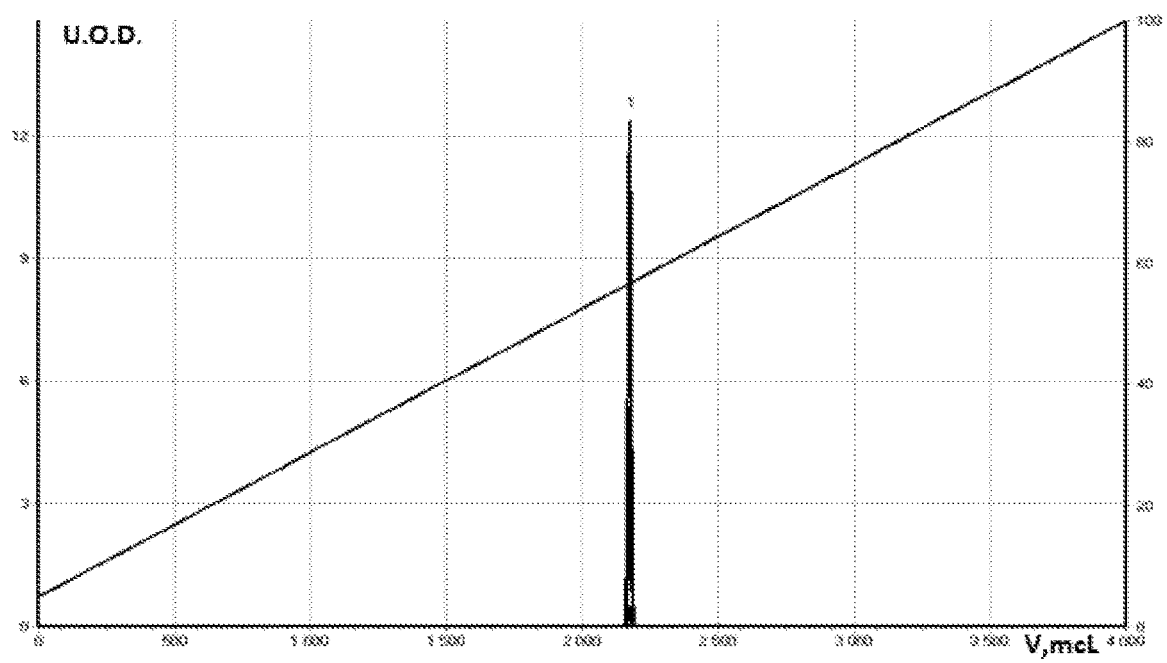
FIG. 4. HPLC (Milichrome A-02) pentaacetyl-quercetin (IVb), gradient solution A: 0.5 M lithium perchlorate/0.1 M perchloric acid, solution B: acetonitrile (B from 5% to 100%)
Figure 5:
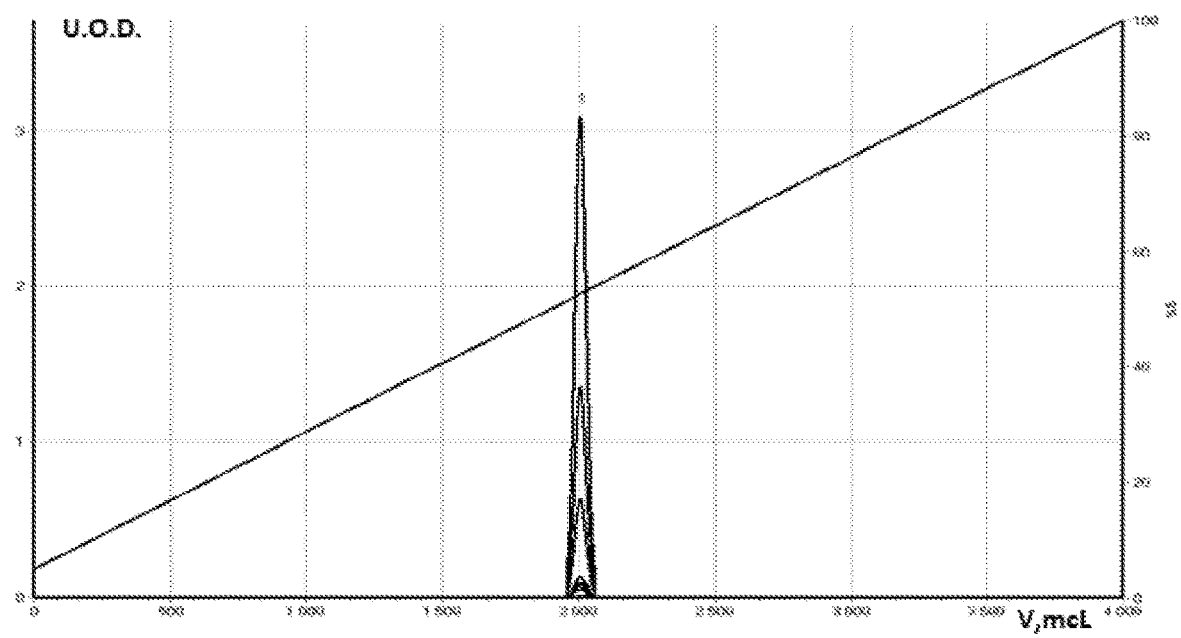
FIG. 5. HPLC (Milichrom A-02) combinatorial supramolecular derivative of quercetin (IVd), gradient solution A: 0.5 M lithium perchlorate/0.1 M perchloric acid, solution B: acetonitrile (B from 5% to 100%)

10 mM quercetin (I) is dissolved in 10 ml of dioxane, 50 mM acetic anhydride (II) is added, the solution is stirred and heated under reflux for 20 minutes. The solution is poured into ampoules and lyophilized
NMR H1 pentaacetyl quercetin (IVb): s: 7.68; 7.63; 7.03; 7.1; 7.6; 6.02; 5.94; m 2.12-2.4 HPLC (Milichrom A-02; Gradient HClO4/LiClO4: AcCN 5-100%):

FIG. 2 shows the chromatogram of the initial quercetin (I), 2b-combinatorial modified with two anhydrides (IVd) (FIG. 2). FIGS. 3-4 show HPLC chromatograms of two derivatives: fully succinylated (IVc) and fully acetylated quercetin (IVb), respectively, as control samples. As can be seen from the graphs, the retention time (volume) of the derivatives differs both from the original quercetin and among themselves. In addition, at the same concentration of quercetin, the peak area and the width of its base are larger, which indicates that these are derivatives of quercetin and that there are several of them. The differences between the retention volume (I), (IVb) and (IVc) indicate the completion of the reaction of complete succinylation and acetylation in the structure of quercetin, respectively.

Fully succinylated and fully acetylated quercetins did not exhibit biological activity.

Example 4. Obtaining Pharmaceutical Compositions Based on a Combinatorial Derivative of Quercetin The task is achieved based on the pharmaceutical composition with anti-inflammatory, cardio- and angioprotective activity, it contains bioflavonoid quercetin in the form of combinatorial modified derivatives (CMQ obtained as shown in example 1), contains chlorophyllipt, enhancing its pharmacological action, reducing toxicity and side effects, and also targeted additives that CMQ contribute to the formation of pharmaceutical dosage forms. According to the invention, CMQ, is the main active agent is introduced in an amount of 0.5-20%, polyvinylpyrrolidone and is used as a solubilizer, sodium laurisulfate is a surface-active substance, as the main components of the pharmaceutical composition, when a certain technological operation and mechanochemical interaction to form a complex with the studied pharmaceutical and pharmacological properties.

Moreover, in the pharmaceutical composition, chlorophyllipt is contained in an amount of between 2 to 7%. Instead of chlorophyllipt, another cuprophillin, chlorophyllin, can be used. In this case, CMQ in the composition contains an amount of from 50 to 70%. The substances are pre-dissolved in ethanol together with lecithin or TWEEN- 80, and ethanol is distilled off by heating or under vacuum. In addition, as the target additives, the solubilizer polyvinylpyrrolidone in the amount of 10-50% and the surface-active agent sodium lauryl sulfate in the amount of 0.25-10% were selected. In this case, the fillers contain at least one binding agent, one baking powder and one lubricating agent. Moreover, microcrystalline cellulose in the total amount of 10-20% was selected as a binding agent. Moreover, croscarmellose sodium salt in the total amount of 1-15% was selected as a baking powder. Moreover, magnesium stearate in the total amount of 0.25-5% was selected as a lubricant. In addition, the pharmaceutical composition is in the dosage form of tablets coated with a polymer film or capsules.

The task is also achieved by the fact that in the method for producing a pharmaceutical composition with anti-inflammatory, cardio and angioprotective activity according to the invention, preliminarily chlorophyllipt, CMQ (IVd) and target additives are mixed, compacted, milled, the resulting mixture is mixed with pharmaceutically acceptable excipients, then this mixture dry or wet granulation is carried out, and then hard gelatin capsules are filled with granulate or compressed and the tablets are coated with a polymer film. According to the invention, the developed method for producing a pharmaceutical composition allows one to obtain dosage forms with a complex pharmaceutical composition in the form of coated tablets or capsules 10 containing components in such a quantitative range, in %:
Chlorophyllipt Dense Extract 5-25%
CMQ (IVd) 10-40%
Fillers up to 100%

Both active substances of the new pharmaceutical composition were combined in it, taking into account the knowledge about their pharmacological and therapeutic properties obtained with the use of monopreparations based on their substances. Selected target additives, due to their physicochemical properties, contribute to the solubilization of active substances and their sufficiently high dissolution in the aqueous physiological environment of the gastrointestinal tract. The anti-inflammatory and atherosclerotic effect of CMQ (IVd) has a somewhat non-traditional mechanism, which is based on pronounced antileukotriene activity. However, it should be noted that many other positive properties of the initial quercetin allow us to predict its indispensability in the correction of the inflammatory process and the relevance of the composition of the composition with chlorophyllipt. The feasibility of using CKPV (IVd), taking into account its pharmacodynamics, in such a new drug is obvious.

The mechanism of anti-inflammatory action of CKPV (IVd) is schematically reduced to the inhibition of 5-lipoxygenase (LOG-5), a key enzyme in the biotransformation of arachidonic acid beyond the lipoxygenase pathway of metabolism. The biochemical transformation of arachidonic acid ends with the formation of end products—leukotrienes, which determine the occurrence of inflammatory processes. Thus, by blocking by quercetin of the further stage of leukotriene synthesis provides inhibition of these negative processes. At the same time, leukotrienes are characterized by a decrease in the intensity of blood supply to organs, activation of lipid peroxidation (LPO). Quercetin and CMQ (IVd), respectively, are characterized by angioprotective, vasodilator, anti-inflammatory, hepatoprotective, choleretic action. It is able to reduce the intensity of the processes of free radical oxidation of lipids, proteinuria, hyperglycemia and also exhibit hypoazotemic and diuretic effects.

Quercetin, having an anti-leukotriene effect, prevents damage to the vascular endothelium of the ischemic site and reduces postischemic microcirculation disorders—pathological conditions caused by leukotrienes. Thus, quercetin protects the vascular endothelium not only from such factors of aggression induced by ischemia, as LP, and from leukotrienes. Quercetin, in contrast to traditional NSAIDs, not only does not exhibit ulcerogenic effects, but vice versa, creates a gastroprotective effect due to the ability to suppress the functioning of H+—K+-ATPase (decrease in the synthesis of hydrochloric acid). It is also able to stimulate the production of cytoprotective prostaglandin E2 by the cells of the gastric mucosa and reduce the number of reactive oxygen species in the tissue of the gastric wall. The combined drug NAM with CKPV (IVd) is unknown. The combination in one dosage form of two active substances with different physicochemical properties is a rather difficult task for pharmacy.

The solution of the problem in technical terms was carried out by the consistent development of the manufacturing technology of the pharmaceutical composition and in accordance with the pharmacopoeial methods of its research. First of all, the pharmaceutical development of the pharmaceutical composition began with an assessment of the physico-chemical properties of DNs and CMQ (IVd), primarily focusing on their ability to emulsify in aqueous media so that these active substances have maximum bioavailability when administered orally in physiological conditions of the stomach substances is possible only with the use of excipients with properties.

It was possible to achieve high solubility using solubilizers and surface-active substances. Such solubility modulators are polyvinylpyrrolidone (povidone, GTVP) and sodium lauryl sulfate (LSH), TWEEN-80 and lectin, the quantitative values of their introduction into the pharmaceutical composition were determined during the pharmaceutical development of the composition, focusing on the solubility profiles of the samples, performing the solubility test. Studying the kinetics of dissolution of samples of the pharmaceutical composition, both granules for capsules and tablets, with variable mass values of PVHT, LSN, TWEEN-80 and lecithin, their optimal ratio with CMQ (IVd) was established.

It is known that, due to the absence of the crystal structure of CMQ (IVd), the solubility of its substance is very low (1 mg in 100 ml of water). By combining it with PVP by means of mechanochemical interaction, that is, by pressing (compacting) the initial granulate, it was possible to increase the solubility of CMQ (IVd) to 200 mg in 100 ml of water. Thus, the obtained complex CMQ (IVd) with PVP is almost equally soluble in aqueous solutions with different pH values, which, after pharmaceutical requirements, imitate the physiological environment of the body.

TABLE 1

Composition and ratio of ingredients in one capsule or tablet core of the Greenflof pharmaceutical composition.

| No. p/p 1 | Name of ingredients 2 | mg 4 | % 5 |
|---|---|---|---|
| 1 | Liposomes CMQ (IVd) | 40.00 | 20.00 |
| 2 | Polyvinylpyrrolidone K-25 | 40.00 | 20.00 |
| 3 | Thick Chlorophyllipt Extract | 25.00 | 12.50 |
| 4 | Microcrystalline cellulose | 80.00 | 40.00 |
| 5 | TWEEN-80 | 10.00 | 5.00 |
| 6 | Cholecalciferol | 3.00 | 1.50 |

TABLE 1-continued

Composition and ratio of ingredients in one capsule or tablet core of the Greenflof pharmaceutical composition.

| No. p/p 1 | Name of ingredients 2 | mg 4 | % 5 |
|---|---|---|---|
| 6 | Magnesium stearate | 2.00 | 1.00 |
| | Content of capsule or tablet core: | 200.00 | 100.00 |

To ensure the physicochemical stability of the complex, the weight ratio between CMQ (IVd) and PVP should be in the range 1: 1-1:3. It should be noted that these mass values of PVP are also sufficient to increase the solubility of the substance of MD due to the formation of the corresponding complex compound. The povidones used in their molecular weights differ as follows: K90-1,000,000; K25-30000; C17-10,000. Considering the characteristics of the dissolution kinetics of the complex of quercetin with PVP, a sufficient amount of LSF, a surfactant, was selected that promotes the rapid and uniform wetting of the surface of the complex granulate. This also reflected in accelerating the dissolution of the complex in the initial periods of time and, thus, could create optimal conditions for the absorption by the walls of the stomach of the soluble form of quercetin. With significant hydrophobicity of the surface of the DN crystals, these selected auxiliary substances—PVP and VLF, also contributed to the solubility of this substance, and thereby could increase the bioavailability of this NSAID. A positive effect on the solubility of CMQ (IVd) is also exerted by the selected amount of PVP and VLF, as evidenced by solubility profiles.

All samples of the pharmaceutical composition, starting with a complex of active substances—CMQ (IVd) and MDs with PVP and LSN, were obtained under consecutive technological operations by dry or wet granulation of the ingredients of the complex and auxiliary substances. The prepared granules were used to fill the capsules or they were tableted and the solubility of these dosage forms was studied in accordance with the Pharmacopoeia Dissolution test. The solubility characteristics of DNs and CMQ (IVd) in the pharmaceutical composition indicated a significantly higher solubility of these active 10 ingredients compared to the solubility of individual substances. In the course of pharmaceutical development, a sample of a pharmaceutical composition of a certain composition was made (see Table 1), named by the authors of GreenFlo and found application in studies of pharmacological properties.

The pharmaceutical composition of the composition obtained in accordance with dry granulation technology includes: mixing active substances with fillers, compacting or briquetting the mixture, grinding, mixing grinding with fillers and granulating, compressing granulate into tablets or filling hard gelatin capsules with it. Wet granulation technology is characterized by a granulation stage of the mixture, where instead of a compactor or press use, wet granulation equipment and a dryer are used, such as a mixer granulator with agitators, such as Rota P or a granulator-dryer of a fluidized bed, such as Hurtling.

We give specific examples of the invention. The following examples illustrate the main aspects of the present invention, but should not be construed as limiting. Obtaining all samples of granules of the complex of active substances—CMQ (IVd) and DN, with PVP was carried out under the conditions of technological operations of granulation by dry or wet method, using dry pressing (compaction) of a mixture of active ingredients, followed by grinding of the briquetted material. Wet granulation was carried out in granulator-dryers in vacuum or warm running air in devices with a pseudo-boiling layer. Capsules were filled into the obtained granules or tableted, examining the solubility of these dosage forms according to the Dissolution test. The solubility characteristics of DNs and CMQ (IVd) in the pharmaceutical composition indicated a significantly higher solubility of the complex of active ingredients in comparison with the solubility of individual substances. Thus, in the course of pharmaceutical development, a sample of the pharmaceutical composition was made, named by the authors of the invention "GreenFlo", which found, as a preparation of a certain composition, the use of toxic-pharmacological properties in research:

TABLE 2

Composition and ratio of ingredients per capsule or tablet of the Greenflo pharmaceutical composition

| No p/p 1 | Name of ingredients 2 | mg 3 | % 4 |
|---|---|---|---|
| 1 | Liposomal polyvinylpyrrolidone CMQ (IVd) | 40.00 | 20.00 |
| 2 | к-25 | 40.00 | 20.00 |
| 3 | Thick Chlorophyllipt Extract | 25.00 | 12.50 |
| 4 | Microcrystalline cellulose | 80.00 | 40.00 |
| 5 | TWEEN-80 | 10.00 | 5.00 |
| 6 | Cholecalciferol | 3.00 | 1.50 |
| 7 | Magnesium stearate | 2.00 | 1.00 |
| 8. | Contents of capsule or tablet core | 200.00 | 100.00 |

The pharmaceutical composition of the above composition obtained by dry granulation technology, including mixing the active substances with excipients, compacting or briquetting the mixture, grinding and mixing it with excipients, and finally granulate it is compressed into tablets or filled with hard gelatin capsules. Wet granulation technology is characterized by a granulation stage of the mixture, where instead of a compactor or press, wet granulation and drying equipment is used, such as a granulator-mixer with agitators, type 25 Rota P or granulator-dryer, such as Huttling with a boiling layer. The following embodiments illustrate aspects of the invention but should not be construed as limiting.

Example 5. A Sample of a Pharmaceutical Composition with Chlorophyllipt

The substances CMQ (IVd), thick extract chlorophyllipt and polyvinylpyrrolidone (K-25) and cholecalciferol are mixed in a granulator and compressed using a compactor. Then, the resulting briquetted mass is ground in a mill, sieved and the previously prepared mixture of microcrystalline cellulose and croscarmellose sodium salt is added to the obtained granulate in a mixer. After 2-3 hours of mixing, cholecalciferol is added to the granulate and then stirring is continued for another 30 minutes. The finished granulate is transferred to fill gelatin capsules or tableting. A sample of the pharmaceutical composition of this composition is shown in Table 3. In the case of tablets, the cores were coated with the finished Colorcon Opadry II film coating mixture. The tests "Disintegration", "Dissolution" and "Dosage uniformity" were carried out in accordance with the state pharmacopoeia.

TABLE 3

Composition and ratio of ingredients of the pharmaceutical composition per capsule or tablet.

| No p/p 1 | Name of ingredients 2 | mg 3 | % 4 |
|---|---|---|---|
| 1. | Liposomes CMQ (IVd) | 40.00 | 17.02 |
| 2. | Polyvinylpyrrolidone K-25 | 80.00 | 34.04 |
| 3. | Thick Chlorophyllipt Extract | 25.00 | 10.63 |
| 4. | Microcrystalline cellulose | 71.00 | 30.57 |
| 5. | Croscarsmellose sodium | 13.00 | 5.53 |
| 6. | Cholecalciferol | 3.00 | 1.27 |
| 7. | Magnesium stearate | 2.15 | 0.91 |
| 8. | Contents of capsule or tablet core | 235.00 | 100.00 |

Example 6. Obtaining Dry Granulate

The substances CMQ (IVd), a thick extract of chlorophyllipt and polyvinylpyrrolidone (polyplasdone K-25), and then cholecalciferol are placed in a Rota P granulator-mixer and stirred for 1.5-2 hours, microcrystalline cellulose and croscarmellose sodium salt are added. The mixture is stirred for 30 minutes, a sufficient amount of purified water is gradually added to it with stirring, the wet granulate is stirred for 2 hours at room temperature. Then granulate is dried by connecting a vacuum and 10 heating, for 3-4 hours. Dry granulate is dusted with magnesium stearate, mixing for 40 minutes, and then transferred to the manufacture of finished dosage forms. Thus, the composition of the sample obtained by the pharmaceutical composition are shown in table 4.

TABLE 4

Composition and ratio of ingredients of the pharmaceutical composition per capsule or tablet

| No p/p 1 | Name of ingredients 2 | mg 3 | % 4 |
|---|---|---|---|
| 1. | Liposomes CMQ (IVd) polyvinylpyrrolidone | 40.00 | 13.33 |
| 2. | к-25 | 140.00 | 46.67 |
| 3 | Thick Chlorophyllipt Extract | 25.00 | 12.50 |
| 4. | Microcrystalline cellulose | 65.50 | 21.83 |
| 5. | Lecithin + TWEEN-80 | 21.00 | 7.00 |
| 6. | Cholecalciferol | 5.00 | 1.67 |
| 7. | Magnesium stearate | 3.50 | 1.17 |
| 8. | Contents of capsule or tablet core | 300.00 | 100.00 |

Example 7. Obtaining a Liposomal Suspension Form for the Further Preparation of Urananulate, Tablet Mass and Tablet Forms of CCV In 80-200 ml of 96% ethanol, 2-20 g of CMQ (IVd), 1-3 g of cholecalciferol, 1-7 g of a thick extract of chlorophyllipt and 20-50 g of phosphatidylcholine are dissolved, then ethanol is distilled off under vacuum, 50 ml of distilled water are added to the resulting mixture and sonicated at 44 kHz for 15-50 minutes, the obtained suspension of liposomes is dried in freeze drying, and the resulting powder is used as shown in the previous examples to obtain tablet forms. The size of liposomal nanoparticles in ultrasonic emulsification is 120-300 nm. If milk powder is used instead of lecithin, the particle size will be 500-1000 nm.

A preclinical study of the pharmaceutical composition was carried out using the GreenFlo sample in the study tests in order to establish in full the toxicological and pharmacological properties of the future drug, which could become a promising drug.

Example 8. Oral Toxicity Studies of GreenFlo

Experimental studies were carried out according to the method of V. B. Prozorovsky in the dose range of 500-1500 mg/kg according to the amount of active substances, with the intragastric administration of GreenFlo to mice and rats. Observations of animals were carried out within two weeks after administration of the drug. The results of the study are shown in table 5.

TABLE 5

Mortality rates in the study of acute toxicity of Greenflo (n = 72)

| | Lethal effect, death of animals/number of animals | | Average lethality, % | |
|---|---|---|---|---|
| Dose | mice | rats | mice | rats |
| 500 | 0/6 | 0/6 | 0 | 0 |
| 700 | 1/6 | 1/6 | 16.7 | 16.7 |
| 900 | 2/6 | 3/6 | 33.3 | 50.0 |
| 1100 | 3/6 | 4/6 | 50.0 | 66.6 |
| 1300 | 4/6 | 5/6 | 66.7 | 83.3 |
| 1500 | 6/6 | 6/6 | 100 | 100 |

The average lethal dose of GreenFlo was calculated based on the dependence of the lethality rate on the used dose by the probit analysis method. As a result of calculations, it was determined that LD5 0 GreenFlo for mice is 1051.3±52.5 mg/kg (404.2 mg/kg for cholecalciferol), and for rats −952.5±45.2 mg/kg (366 5 mg/kg for cholecalciferol). Thus, the results of studying the toxicological characteristics of GreenFlo in mice and rats make it possible to classify this agent as a class of low toxic substances (501 mg/kg<LD5 0>5000 mg/kg), according to the generally accepted classification of toxicity according to K. K. Sidorov.

Example 9. The Study of Medium-Effective Doses of Greenflo in Development Experimental Inflammation—The Main Promoter of Atherosclerosis and its Complications The study of medium-effective doses of Greenflo was carried out on a model of carrageenan edema extremities in rats using the drug in doses of 5, 10 and 20 mg/kg according to the amount of active substances, which corresponds to approximately 1/200, 1/100 and 1/50 of LD5 0. The EDS 0 index was determined by the probity analysis of the activity-dose dependence as 3 hours after the introduction of phlogogen. The results of the study are shown in table 6.

TABLE 6

The effect of Greenflot on the course of carrageenan edema of the foot in rats 3 hours after administration to the phlogogen (n = 40)

| Experimental group | Dose mg/kg | The increase in the foot volume, cu | Antiexudative activity, % |
|---|---|---|---|
| Control pathology | | 36.7 ± 2.0 | – |
| Greenflow | 5.0 | 33.2 ± 1.2 | 9.2 ± 0.4 |
| Greenflow | 10.0 | 23.5 ± 0.9* | 36.1 ± 1.3 |
| Greenflow | 20.0 | 17.6 ± 0.7* | 52.2 ± 2.2 |

Note.

TABLE 6-continued

The effect of Greenflot on the course of carrageenan edema of the foot in rats 3 hours after administration to the phlogogen (n = 40)

| Experimental group | Dose mg/kg | The increase in the foot volume, cu | Antiexudative activity, % |
|---|---|---|---|

*P < 0.05 relative to the control pathology group.

In the course of the calculations, Greenflo EDS 0 was determined by antiexudative activity, which amounted to 18.24±2.06 mg/kg by the amount of active substances, which corresponds to 7.02±0.79 mg/kg according to the control NSAID—sodium diclofenac (DN)

According to the results of a study of acute toxicity and medium-effective doses of Greenflo, the therapeutic index (TI) was calculated, which characterizes the breadth of the therapeutic effect of the drug (Table 7).

TABLE 7

Characterization of the breadth of the therapeutic effect of Greenflo

| Substance | ED 50, mg/kg | LD 50, mg/kg | TI | Relative TI to DN |
|---|---|---|---|---|
| Greenflow | 18.2 | 952.5 | 523 | 4.4 |
| DN | 8.0 [14, 16] | 95.0 [17] | 11.9 | 1 |

The calculation results indicate a significantly wider therapeutic effect of the studied drug compared to DN, which is due to both a decrease in toxicity and a higher Greenflo activity, which, in turn, is due to the summation of the pharmacological effects of both substances and confirms the advisability of creating a combined dosage form on their basis.

Example 10. The Study of Anti-Alterative Activity of Greenflo on the Model of Scarified Wounds in Rats The study of the anti-alterative properties of Greenflo was carried out on a model of standard scarified wounds in rats as compared with the monocomponents of the composition—CMQ liposomes (IVd) and chlorophyllipt. Antialterative activity of drugs evaluated by their effect on wound area reduction indicators. The results of the study are shown in table 8.

TABLE 8

Anti-alterative activity of Greenflo, % (p = 40)

| Research drug | Dose mg/kg | 7 days | 9 days | 11 days | 13 days | 15 days |
|---|---|---|---|---|---|---|
| Greenflo | 18.2 | 32.75 ± 0.87* | 52.09 ± 1.39* | 58.06 ± 1.55* | 79.26 ± 2.11* | 100.0 |
| CMQ (IVd) | 11.2 | 16.52 ± 0.44 | 17.87 ± 0.48 | 27.96 ± 0.75 | 31.85 ± 0.85 | 48.86 ± 1.3 |
| chlorophyllipt | 7.0 | 10.72 ± 0.29 | 12.17 ± 0.32 | 15.05 ± 0.40 | 14.81 ± 0.4 | 4.55 ± 0.12 |

Note.
*P < 0.05 relative to animals receiving reference substances.

The results obtained indicate a significantly higher level of Greenflo activity compared to its monocomponents, since complete wound healing and, correspondingly, a 100% level of antialterative effect of the studied drug were recorded on the 15th day of the experiment. In terms of alternative activity indicators, Greenflo significantly exceeded CMQ (IVd) and thick chlorophyllipt extract by 2.0-2.9 and 2.2-5.4 times, respectively. Therefore, Diclocor has a positive effect on alternative inflammation in the model of scarified wounds in rats, helping to accelerate the rate of wound healing, reduce the area of wounds and exhibit significantly higher rates of alternative activity compared to quercetin and DN.

Example 11. The Study of the Antiproliferative Properties of Greenflo on the Model of "Cotton" Granuloma in Rats Greenflo's antiproliferative activity was studied using a "cotton" granuloma model in rats compared to the action of the monocomponents of the studied agent. The results of the study are presented in table 9.

TABLE 9

Greenflo antiproliferative activity on the model of "cotton" granuloma in rats (n = 40)

| Experimental group | Dose mg/kg | The amount of granulation tissue, mg | Activity, % |
|---|---|---|---|
| Control pathology | — | 45.2 ± 1.7 | — |
| Greenflow | 18.2 | 34.3 ± 1.3*/• | 24.12 ± 0.88**/• |
| CMQ (IVd) | 11.2 | 37.0 ± 1.4* | 18.14 ± 0.66 |
| Chlorophyllipt | 7.0 | 39.1 ± 1.4* | 13.50 ± 0.49 |

Notes:
*p ≤ 0.05 relative to the control pathology;
**p ≤ 0.05 relative to animals receiving CMQ IVd);
3) •p ≤ 0.05 relative to animals treated with chlorophyllipt.

The data of the studies showed that in terms of the degree of antiproliferative activity, Greenflo significantly exceeds the action of CMQ (IVd) by 1.3 times and chlorophyllipt by 1.8 times. Thus, under the conditions of the development of proliferative inflammation, Greenflo has a pronounced antiproliferative effect, which is very useful in terms of treating inflammatory and destructive diseases of parenchymal organs such as the liver, kidneys, heart, etc., since it can help suppress the development of sclerotic processes in them.

Example 12. An in-Depth Study of the Antiproliferative Properties of Greenflo on a Model of Doxorubicin Cardiomyopathy in Rats An in-depth study of the antiproliferative properties of Diclocor was carried out under conditions of the development of doxorubicin-induced plastic myocardial insufficiency in rats, reproducing it by intraperitoneal administration of doxorubicin at a dose of 20 mg/kg. During the experiment, on the 10th day, the effect of Greenflo on some biochemical parameters of laboratory animals was evaluated in comparison with the activity of MDs in an equivalent dose (Table 10).

TABLE 10

The effect of Greenflo on some biochemical parameters of rats with doxorubicin cardiomyopathy (n = 31)

| Experimental group | Blood ASAT, mmol/year * L | LDH blood, mmol/year * L | TBA blood reactants, μmol/L | Myocardial TBA Reactants, μmol/g |
|---|---|---|---|---|
| Intact control (n = 12) | 0.63 ± 0.03 | 5.10 ± 0.23 | 2.27 ± 0.07 | 63.60 ± 1.82 |
| Control pathology (n = 4) | 1.51 ± 0.12* | 7.75 ± 0.71* | 4.25 ± 0.28* | 151.61 ± 8.62* |
| Greenflo 18.2 mg/kg (n = 9) | 0.82 ± 0.06*/**/* | 5.97 ± 0.35*/** | 3.59 ± 0.11*/** | 97.20 ± 3.40*/**/• |
| Chlorophyllipt 7.0 mg/kg (n = 6) | 1.33 ± 0.07* | 6.85 ± 0.42* | 4.02 ± 0.21* | 136.63 ± 6.7* |

Notes:
*P ≤ 0.05 relative to intact animals;
**p ≤ 0.05 relative to the control pathology group;
•p ≤ 0.05 relative to animals receiving NAM.

The results of biochemical studies showed an inhibitory effect on the part of the studied drugs on the accumulation of lipid peroxidation products and the growth of fermentemia in the development of cardiomyopathy. Greenflo showed the most significant therapeutic effect, which is confirmed by the likely dynamics of indicators relative to the control pathology. At the same time, the activity of AsAT and the content of TBA-reactants in the myocardial tissue were significantly lower than in animals treated with DNs—1.7 and 1.4 times, respectively. Thus, the obtained data indicate that Greenflo has, in addition to anti-inflammatory, also cardioprotective properties, which makes it expedient to use it in the treatment of inflammatory and destructive myocardial diseases.

Example 13. The Study of the Effect of Greenflo on the Course of Experimental Autoimmune Arthritis The study was conducted on a model of collagen-induced arthritis in rats, which was reproduced by subcutaneous twofold administration (with an interval of a week) of an emulsified mixture of bovine collagen type II and Freund's complete adjuvant (1:1) at a dose of 2 mg/kg for collagen [22]. During the study, in the blood serum of 10 animals, the dynamics of the content of necosanoids (prostaglandin E2 (PGE2), 6-keto-prostaglandin F1a (6-keto-PGF 1α), thromboxane B2 (TxB2) and leukotriene B4 (LTB4) was evaluated on the 28th day. using enzyme-linked immunosorbent assay kits manufactured by Neogen Corporation (USA). Greenflo efficacy was studied in comparison with the action of its monocomponents in equivalent doses. The results of the study are shown in table 11.

TABLE 11

The effect of Greenflot on the content of eicosanoids in the blood serum of rats with collagen-induced arthritis (n = 50)

| Experimental group | PGE2, пг/мл | 6-keto-PGF1α, пг/мл | TxB2, пг/мл | LTB4, пг/мл |
|---|---|---|---|---|
| Intact control | 879.8 ± 12.5 | 261.6 ± 4.2 | 242.6 ± 9.5 | 261.4 ± 6.3 |
| Control pathology | 1248.4 ± 26.1* | 294.3 ± 4.1* | 493.2 ± 4.8* | 421.3 ± 4.7* |
| Greenflo 18.2 mg/kg | 901.5 ± 17.5**/• | 272.5 ± 6.7** | 256.6 ± 8.9**/' | 345.6 ± 3.1*/**/•/•• |
| CMQ (IVd) 11.2 mg/kg | 1198.7 ± 22.1* | 286.8 ± 7.4* | 472.7 ± 6.7*/** | 282.9 ± 8.4** |
| Chlorophyllipt liposomal/in milk 7.0 mg/kg | 925.5 ± 13.6*/** | 279.2 ± 5.4*/** | 265.4 ± 5.9** | 398.3 ± 6.5*/** |

Notes:
*p ≤ 0.05 relative to intact animals;
**p ≤ 0.05 relative to control animals;
•p ≤ 0.05 relative to animals treated with quercetin;
4) ••p ≤ 0.05 relative to animals receiving NAM.

In the course of the study, it was found that the use of Greenflow against the background of the development of collagen-induced arthritis contributes to the probabilistic normalization of the content of eicosanoids in rat serum. So, the level of PGE2 decreased by 1.4 times; the content of 6-keto-PGF1α—1.1 times; TxB2- 1.9 times and the level of LTB4-1.2 times. Moreover, Diclocor exceeded the comparison drugs Quercetin and chlorophyllipt in the degree of pharmacological effect on most of the studied parameters. The results obtained indicate that the Greenflo drug has a complex mechanism of action with effects both the cyclooxygenase (due to the content of chlorophyllipt) and lipoxygenase (the presence of CMQ (IVd) metabolic pathways of arachidonic acid. In this case, Greenflo is a promising corrector of inflammatory and destructive joint diseases with an autoimmune component, such as rheumatoid arthritis.

Example 14. Study of the Effect of Greenflo on the Structure of Articular Cartilage in the Development of Experimental Osteoarthritis The effect of Greenflo on the morphostructure of articular tissues on the background of the development of experimental osteoarthritis was studied in comparison with the action of its monocomponents in equivalent doses. The studies were performed on a model of systemic steroid arthrosis in rats, which was reproduced by three intramuscular injections of dexamethasone at a dose of 7 mg/kg with an interval of one week. The test agents were administered daily for 1 month, starting 2 weeks after the last injection of dexamethasone. During the morphological study of micro preparations of articular cartilage as of the 56th day of the experiment, morphometric determinations of its thickness, density of chondrocyte location and semi-quantitative assessment of the state of its main structures were performed (Table 12).

TABLE 12

Morphometric indicators of the articular cartilage of rats with experimental osteoarthrosis under the influence of Greenflo (n = 50)

| Study group | Cartilage thickness, conditional. units | Cell density according to the condition. units square | The amount of points on the system for assessing the condition of cartilage |
| --- | --- | --- | --- |
| Intact control | 15.33 ± 1.15 | 42.40 ± 5.64 | 24.46 ± 0.22 |
| Control pathology | 12.62 ± 0.58* | 28.63 ± 1.85* | 12.68 ± 0.85* |
| Greenflo 18.2 mg/kg | 15.73 ± 0.59**/* | 35.83 ± 4.31*/** | 20.19 ± 0.93*/**/* |
| CMQ (IVd) 11.2 mg/kg | 15.66 ± 1.35 | 32.67 ± 2.48* | 18.09 ± 0.94*/**/• |
| Lipsomal chlorophyllipt/ milk based 7.0 mg/kg | 13.77 ± 0.52 | 32.20 ± 3.02* | 14.66 ± 0.95* |

Notes:
*$p \leq 5.05$ for relatively intact animals;
**$p \leq 0.05$ relative to the control pathology group;
•$p \leq 0.05$ relative to animals that received NAM.

The results of the studies indicate that under the conditions of the development of experimental osteoarthritis under the influence of Greenflo, there is a significant increase in the thickness of the articular cartilage and the density of the location of the chondrocytes on average by 20%, %, as well as the total score for a semi-quantitative system for assessing the state of cartilage tissue 1.6 times. It should be noted that for most of these parameters, Greenflo significantly exceeded the activity of chlorophyllipt and without significant differences—CMQ (IVd). All of the above indicates the presence of certain chondroprotective properties of Greenflo, determined by the content of CMQ (IVd) in its composition. The use of CMQ (IVd) in the composition of Greenflo allows positively modifying the effect of chlorophyllipt on the cartilage tissue and significantly expanding the possibilities of its use against the background of the development of degenerative-dystrophic joints lesions.

Example 15. Antihypertensive Activity of Greenflo

Two groups of white rats, 5 animals each, were administered intravenously at a dose of 0.0025 mmol/kg octadine and a Greenflo liposomal suspension (in terms of chlorophyllipt), and then the dynamics of the SBP was observed for 3 hours. The antihypertensive effect of the drugs was evaluated after 3 hours of observation. The results obtained were statistically processed using Student's t criterion and are given in table. thirteen. Digital data table. 13 show that Greenflo in an equimolecular dose lowers the SBP in normotensive white rats 2 times more than octadine. That is, under the action of octadine, the hypotensive effect averaged 19.7±2.2%, and under the action of Greenflo, the hypotensive effect averaged 36.8±3.1%.

TABLE 13

The effect of Greenflot and octadine on the SAD of white rats

| A drug | Dose of the drug | | Antihypertensive effect, % |
| --- | --- | --- | --- |
| | in mg/kg | in mmol/kg | |
| Octadine | 6.2 | 0.025 | 19.7 ± 2.2 |
| Greenflo | 5.0* | 0.025* | 36.8 ± 3.1 |

*In terms of the amount of thick extract of chlorophyllipt

In order to compare the antihypertensive activity of Greenflo and octadine in rabbits, two groups of animals of 5 rabbits of both sexes were injected intravenously with Greenflo and the dynamics of the GARDEN for 3 hours. The results of the experiments are given in table. 14.

TABLE 14

Comparative antihypertensive activity of Greenflo and octadine in rabbits.

| A drug | Dose of the drug | | Antihypertensive effect, % |
| --- | --- | --- | --- |
| | in mg/kg | in mmol/kg | |
| Octadine | 15.0 | 0.06 | 32.0 ± 6.1 |
| Greenflo | 10.0 | 0.05 | 29.0 ± 5.6 |

Therefore, in rabbits, to achieve a statistically equal, within 30%, hypotensive effect, octadine 15 mg/kg was required, or 0.01 mmol/kg more than Greenflo.

To comparatively evaluate the anti-hypotensive activity of Greenflo on cats, two groups of five animals each were injected with Greenflo and Octadin liposome suspension and the dynamics of systemic blood pressure was recorded for 3 hours. The results of the experiments are presented in table. 3.

Data in table 15 shows that in cats, to achieve a statistically equal hypotensive effect (within 30%), octadine 20 mg/kg was required, which is a dose of 0.08 mmol/kg. This exceeds the Greenflo dose by 0.03 mmol/kg and suggests that GreenFlo has significantly greater antihypertensive activity than octadine.

TABLE 15

Comparative antihypertensive activity of Greenflo in cats

| A drug | Dose of the drug | | Antihypertensive effect, % |
|---|---|---|---|
| | in mg/kg | in mmol/kg | |
| Octadine | 20.0 | 0.08 | 35.0 ± 9.9 |
| Greenflo | 10.0 | 0.05 | 36.2 ± 6.3 |

For an objective comparison of the activity of the studied substances, ED30 was experimentally established (a unit of action that causes a decrease in SBP by 30%) for each drug. For this purpose, the value of the hypotensive effect of various doses of substances in three groups of five white rats was determined in experiment, the arithmetic mean of the obtained series and their standard errors were calculated. Then, digital data was plotted and ED30 was calculated.

The results are presented in table #16.

TABLE 16

The dependence of the "dose-effect" and ED30 hypotensive effect of Greenflo and octadine

| A drug | Dose mg/kg | The effect, % | ЕД$_{30}$ | |
|---|---|---|---|---|
| | | | мг/кг | ммол/кг |
| Octadine | 5.0 | 18.0 ± 2.7 | — | — |
| Octadine | 10.0 | 26.0 ± 1.5 | — | — |
| Octadine | 20.0 | 33.0 ± 4.9 | — | — |
| Octadine | — | — | 11.2 | 0.045 |
| Greenflo | 1.5 | 17.6 ± 2.7 | — | — |
| Greenflo | 3.0 | 25.2 ± 2.9 | — | — |
| Greenflo | 5.0 | 36.8 ± 3.1 | — | — |
| Greenflo | — | — | 4.0 | 0.02 |

As the data in table. 16, Greenflo hypotensive activity exceeds that of octadine by more than 2 times. The ED30 hypotensive effect of Greenflo is 4.0 mg/kg or 0.02 mmol/kg in terms of chlorophyllipt thick extract.

An indicator of the true hypotensive effect of a new chemical is its ability to lower pathologically elevated SBP. To solve this problem, 5 adult white rats with spontaneous hypertension (weight 260-280 g) were used, in which, before the experiment, the level of SBP averaged 180±1.7 mm Hg. For comparison, an experiment was conducted on 5 white rats with normal SBP. The results of the experiments are presented in table. 17.

TABLE 17

Anti-hypertensive effect of Greenflo in white rats (5 mg/kg)

| Experiment Stages | Source SAD, mmHg | Antihypertensive effect | |
|---|---|---|---|
| | | mmHg. | % |
| Rats with spontaneous hypertension | 180 ± 1.7 | 69.6 ± 5.1 | 38.6 ± 2.47 |
| Normotensive rats | 119 ± 1.6 | 44.4 ± 3.7 | 37.0 ± 2.72 |

The data table. 17 show that Greenflo at a dose of 5 mg/kg lowered the systemic arterial pressure in "hypertensive" white rats by 69.6±5.1 mm Hg, i.e. 1.57 times more than that of "normotensive" rats (44.4 mmHg). This suggests that Greenflo is a true hypotonic.

The invention claimed is:

1. A composition, comprising:
   a combinatorial quercetin derivative; wherein the combinatorial quercetin derivative is obtained by a combinatorial modification of quercetin by at least a first alkylating and/or acylating modifier and a second alkylating and/or acylating modifier, wherein the first alkylating and/or acylating modifier and the second alkylating and/or acylating modifiers are selected from the group consisting of succinic anhydride, acetic anhydride, maleic anhydride, aconitic anhydride, glutaric anhydride, phthalic anhydride, acetic anhydride, formic acid ethyl ester, monochloroacetic acid, propiolactone, ethylene oxide, methyl chloride, ethyl chloride, and propyl chloride;
   provided that the combinatorial modification of quercetin is performed using a molar ratio of quercetin: first modifier: second modifier of 92:155:155; and the resulting combinatorial quercetin derivative is used as a mixture, without separation into individual components.

2. An emulsified mixture for the preparation of a pharmaceutical and/or cosmetological composition, comprising:
   0.5-10 wt. % of the combinatorial quercetin derivative of claims 1;
   50-70 wt. % foaming agent;
   2-7 wt. % dense extract of chlorophyllipt;
   1.0-3.0 wt. % cholecalciferol; and
   one or more auxiliary substances in an amount to reach a total of 100 wt. %.

3. The emulsified mixture according to claim 2, wherein the foaming agent is phosphotidylcholine present in the mixture in an amount of 50-95 wt. %.

4. The emulsified mixture according to claim 2, wherein the foaming agent is phosphotidylethanolamine present in the mixture in an amount of 50-95 wt. %.

5. The emulsified mixture according to claim 2, wherein the foaming agent is a dry milk present in the mixture in an amount of 50-70 wt. %.

6. The emulsified mixture according to claim 2, wherein the emulsified mixture is enclosed within one or more capsules for use as a pharmaceutical composition.

7. The emulsified mixture according to claim 2, wherein the emulsified mixture is in the form of a solution for use as a pharmaceutical composition.

8. A method of preparing a combinatorial quercetin derivative, comprising:
   treating quercetin with at least a first alkylating and/or acylating modifier and a second alkylating and/or acylating modifier in a molar ratio of quercetin: first modifier: second modifier is 92:155:155 to obtain a combinatorial mixture; wherein the first alkylating and/or acylating modifier and the second alkylating and/or acylating modifiers are selected from the group consisting of succinic anhydride, acetic anhydride, maleic anhydride, aconitic anhydride, glutaric anhydride, phthalic anhydride, acetic anhydride, formic acid ethyl ester, monochloroacetic acid, propiolactone, ethylene oxide, methyl chloride, ethyl chloride, and propyl chloride.

9. The method of claim 8, wherein the combinatorial mixture of the combinatorial quercetin derivative is used without separating the mixture into individual components.

10. A method of cosmetological or pharmaceutical treatment, comprising:
    preparing a combinatorial quercetin derivative by treating quercetin with at least a first alkylating and/or acylating modifier and a second alkylating and/or acylating modifier;

wherein the first alkylating and/or acylating modifier and the second alkylating and/or acylating modifiers are selected from the group consisting of succinic anhydride, acetic anhydride, maleic anhydride, aconitic anhydride, glutaric anhydride, phthalic anhydride, acetic anhydride, formic acid ethyl ester, monochloroacetic acid, propiolactone, ethylene oxide, methyl chloride, ethyl chloride, and propyl chloride;

wherein a molar ratio of quercetin: first modifier: second modifier is 92:155:155; and wherein the resulting combinatorial quercetin derivative is used as a mixture without separating the mixture into individual components;

preparing an emulsified mixture including the prepared combinatorial quercetin derivative, the emulsified mixture having a composition of:

0.5-10 wt. % of the combinatorial derivative of quercetin;

50-70 wt. % foaming agent;

2-7 wt. % dense extract of chlorophyllipt;

1.0-3.0 wt. % cholecalciferol; and one or more auxiliary substances in an amount to reach a total of 100 wt. %; and treating a mammal with the emulsified mixture.

11. The method of cosmetological or pharmaceutical treatment of claim 10, further comprising enclosing the emulsified mixture within one or more capsules; wherein
treating the mammal with the emulsified mixture includes administering the capsules of emulsified mixture to the mammal as a pharmaceutical composition.

12. The method of cosmetological or pharmaceutical treatment of claim 10, wherein treating the mammal with the emulsified mixture includes administering the emulsified mixture topically as a pharmaceutical composition.

13. The method of cosmetological or pharmaceutical treatment of claim 10, wherein the mammal is a human being, and the emulsified mixture is used as a therapeutic for atherosclerosis.

14. The method of cosmetological or pharmaceutical treatment of claim 10, wherein the mammal is a human being, and the emulsified mixture is used as a therapeutic to accelerate healing of wounds.

15. The method of cosmetological or pharmaceutical treatment of claim 10, wherein the mammal is a human being, and the emulsified mixture is used as a therapeutic for skin rejuvenation.

\* \* \* \* \*